United States Patent [19]

Ohkuma et al.

[11] Patent Number: 5,430,141
[45] Date of Patent: Jul. 4, 1995

[54] METHOD FOR PREPARING LOW CALORIE DEXTRIN

[75] Inventors: Kazuhiro Ohkuma, Sanda; Isao Matsuda; Yoshio Hanno, both of Itami, all of Japan

[73] Assignee: Matsutani Chemical Industries Co., Ltd., Hyogo, Japan

[21] Appl. No.: 788,635

[22] Filed: Nov. 6, 1991

[30] Foreign Application Priority Data

Nov. 8, 1990 [JP] Japan .................................. 2-305463

[51] Int. Cl.$^6$ ...................... C08B 37/16; C08B 30/12; C08B 30/00
[52] U.S. Cl. ................................. 536/103; 536/1.11; 127/32; 127/67; 127/70; 127/71; 426/52
[58] Field of Search .................. 536/103, 1.1; 127/32, 127/67, 70, 71; 426/52

[56] References Cited

U.S. PATENT DOCUMENTS

| | | | |
|---|---|---|---|
| 3,086,008 | 4/1963 | Opila et al. | 536/103 |
| 3,928,135 | 12/1975 | Milner | 195/31 R |
| 3,974,032 | 8/1976 | Harjes et al. | 426/661 |
| 4,668,626 | 5/1987 | Kobayashi et al. | 536/103 |
| 5,139,575 | 8/1992 | Matsuda et al. | 127/23 |

*Primary Examiner*—Nathan M. Nutter
*Attorney, Agent, or Firm*—Sughrue, Mion, Zinn, Macpeak & Seas

[57] ABSTRACT

A method for preparing a low caloric dextrin of which caloric value is not more than 280 kcal/100 g is provided using a pyrodextrin prepared by heating a starch to which mineral acid is added. The method comprising the steps of dissolving a pyrodextrin into water, and reacting alpha-amylase on the dextrin.

3 Claims, No Drawings

METHOD FOR PREPARING LOW CALORIE DEXTRIN

BACKGROUND OF THE INVENTION

1. Field of the Invention

The present invention relates to a method for preparing a low calorie dextrin by treating pyrodextrin with enzyme.

2. Description of the Prior Art

In recent years, living standards have improved remarkably in Japan with, in particular, eating habits attaining substantially the same levels as those in Western countries. As a result, the average life span of Japanese people has been prolonged, thereby bringing about a rapidly aging society which, in turn, results in structural changes in disease sharply increasing the diseases of adult people. Thus, promotion of health is now one of the matters of greatest concern. In this connection, the Health and Welfare Ministry of Japan published a proposal of "Guideline of Eating Habits for Promotion of Health" in 1985 with regard to the eating the habits of Japanese people in general, and in which it was pointed out that one of the problems pertaining to Japanese eating habits was "excessive intake of energy."

On the other hand, in various kinds of processed foods, starch itself and most modified starches, such as pregelatinized starch, pyrodextrin, starch derivative, glucose, corn syrup solids and maltodextrin, are actually employed in large quantity. Caloric values of these starch products, however, amounts to about 400 Kcal/100 g, and accordingly only pyrodextrin is known among the starch products as a useful low calorie food material capable of saving the mentioned "excessive intake of energy."

The inventors of the present application have been aggressively engaged in research and development of dietary fibers, and based on the results thereof, already filed a patent application titled "Method for Preparing Dextrin Containing High Percentage of Dietary Fibers" and others. It has been heretofore known that pyrodextrin is a low calorie material, but is not adaptable to be employed as food material due to its stimulative taste and smell, coloring difficulty, etc. The inventors, however, have come to conceive an idea of employing this pyrodextrin as a new food material. To realize this new idea, the inventors have been further aggressively engaged in studies of overcoming the mentioned drawbacks of pyrodextrin aiming at a satisfiable low calorie food material therefrom while maintaining the property of low calorie as it is. The inventors further have attempted to develop means for easy mass production.

SUMMARY OF THE INVENTION

Accordingly, it is an object of the present invention to provide a novel method for preparing a low calorie dextrin.

To accomplish the foregoing object, the method for preparing a low calorie dextrin in accordance with the invention includes the processes of determining conditions to be satisfied by pyrodextrin used as a raw material of the invention; and extracting fraction of digestion by either chromatographic method or organic solvent method if lower calorie is required, thereby obtaining a low calorie dextrin.

The dextrin in accordance with the invention is produced by the following methods:

(1) A method comprising the steps of: heating a a potato starch by treatment with mineral acid thereby obtaining a pyrodextrin; reacting alpha-amylase with the pyrodextrin obtained; and refining the pyrodextrin thus treated with alpha-amylase by filtering according to conventional methods.

(2) A method comprising the steps of: reacting alpha-amylase with an ordinary pyrodextrin; applying glucoamylase to the hydrolyzate; refining the resulting hydrolyzate by filtering; and extracting the low calorie fraction.

Described first is the above method (1).

It is required to use a quite limited kind of pyrodextrin as a raw material. That is, only a potato starch is qualified as starch material. It is essential to add a mineral acid as a catalyst in the heating step. Various mineral acids are known, and from the viewpoint of use in food, it is particularly desirable to adopt hydrochloric acid. In the pyrodextrin thus obtained, caloric value should be not more than 280 Kcal/100 g in view of its application to prepare a low calorie food. In other words, pyrodextrin whose content corresponds to not more than 70% of 400 Kcal/100 g of ordinary starch or starch product should be used as the raw material. In this respect, it is to be noted that caloric value of white dextrin popularly used in the food and medical field exceeds far from the mentioned 280 Kcal/100 g, and is not suitable for the purpose of achieving low calorie. On the other hand, if the caloric value is less than 220 Kcal/100 g, the food even though hydrolyzed with alpha-amylase exhibits somewhat stimulative taste. Moreover, the load in the refining step after hydrolysis with alpha-amylase is enhanced thereby making it impossible to carry out mass production. Thus, such dextrin of excessively low caloric value is not suitable, either.

Various alpha-amylases can be widely employed in the present invention, including bacterial alpha-amylase. From the viewpoint of reducing calorie value of dextrin as in the object, it is particularly preferable to use alpha-amylase sold under the tradename "Termamyl" and the alpha-amylase sold under the tradename "Klaistase T-5".

The low calorie dextrin thus obtained has usually a caloric value within a range of not more than 280 Kcal/100 g and not less than 220 Kcal/100 g which is quite preferable as a low calorie food material.

Potato starch treated with mineral acid and heated according to normal methods is preferably employed as a pyrodextrin treated with mineral acid to be used in the mentioned method (1). As for the amount of mineral acid, about 1% aqueous solution is added to the starch by several percent (3 to 10%). To satisfy the heating requirement, considering that an acidified aqueous solution was already added, the starch and acid are evenly mixed by stirring and aging in a mixer or disintegrator, then the mixture is preliminarily dried at 100 to 120% to reduce moisture content to about 5%, and heated at a temperature of 150° to 200° C. for 1 to 4 hours. Treatment of the pyrodextrin with alpha-amylase can be carried out according to conventional methods, and in which about 30 to 45% aqueous solution of pyrodextrin is prepared with its pH adjusted to 4.5 to 6.5, then alpha-amylase is added to the pyrodextrin by 0.05 to 0.2%, and the pyrodextrin is held for 30 min to 2 hours at 85° to 100° C., i.e., a reaction temperature of alpha-amylase (this temperature depends on the type of alpha-amylase). In the next step, reaction of alpha-amylase is suspended by increasing the temperature to about 120° C. (i.e., deactivation temperature of alpha-amylase). After completing the reaction of alpha-amylase, activated charcoal is added for the purpose of removing insoluble matter, color, etc. Then filtration is carried out by means of conventional filter press, precoat filter, or the like. Thereafter, salts and coloring matter in the solution are removed by ion exchange resins. Usually, a cation exchange resin, an anion exchange resin and a mixed bed of both types are applied in this order.

Described now is the mentioned method (2).

In this method, not only pyrodextrin prepared from potato starch but also other pyrodextrins can be widely employed. Any other pyrodextrin prepared from various starches, such as corn starch, tapioca starch and the like can be employed. Treatment with alpha-amylase is carried out in the same manner as the foregoing method (1), but in this method (2), after completing such treatment, a further treatment with glucoamylase is required, and in which conventional conditions for such treatment with gluycoamylase are adopted. For example, a solution temperature is reduced to about 55° C. with its pH adjusted to about 5.5, then 0.05 to 0.2% by weight of commercial glucoamylase is added to the original pyrodextrin, and reaction takes place for 24 to 48 hours keeping the solution at this temperature. This reaction is to decompose small molecules such as oligosaccharide existing in the solution to glucose. Then the reaction of glucoamylase is completed at 80° C., for example.

Subsequently, filtration and refining are carried out according to conventional methods.

High calorie fraction is then separated and removed using ion exchange resin by chromatographic method and/or organic solvent method. For that purpose, any commercial strongly acidic cation exchange resin can be widely used.

Preferable examples of commercially available, strongly acidic cation exchange resins are those sold under the tradename Amberlite IR-116, IR118, IR-120B, XT-1022E, XT-471F (all manufactured by Organo), Diaion SK-1B, SK-102, SK-104, SK-106, SK-110, SK-112, SK-116, FR-01 (all manufactured by Mitsubishi Chemicals), and XFS-43281.00, XFS-43280.00, XFS-43279.00, XFS-43278.00 (all manufactured by Dow Chemicals).

These resins are preferably dealt with as alkaline metal type or alkaline earth metal type before their uses. It is preferable to adjust the rate of flow of a column fluid according to the resin used. The rate of flow of the fluid is preferably in the range of S.V.=0.1 to 0.6. A rate of flow out of the above range tends to deteriorate the workability and separability. The temperature at the time of running of the fluid is preferably in the range from 20° C. to 70° C., and a temperature below this range will deteriorate the separability and make the viscosity of fluid increase, thereby yielding negative influence on the fluid, while a temperature exceeding this range will cause the fluid to be colored and deteriorate other quality characteristics.

The mentioned organic solvent method is a separation method using solvent capable of dissolving digestible or low molecular weight components, and accordingly it is preferable to adopt a solvent capable of dissolving low molecular weight components. Preferable as a representative example of such solvent is ethanol.

In the mentioned method (2), since reaction with glucoamylase takes place after hydrolysis with alpha-amylase, not only the pyrodextrin prepared from potato starch is applicable, but also various other pyrodextrins can be equivalently used to obtain a dextrin of desired low caloric value, i.e., not more than 280 Kcal/100 g, more preferably, not more than 220 Kcal/100 g. Since glucoamylase is additionally applied after hydrolysis with alpha-amylase in the method (2), stimulative substances in the object dextrin of not more than 220 Kcal/100 g can also be successfully separated by normal method in the steps of filtration and refining.

Several Experimental Examples are hereinafter described in order to show clearly the features of the present invention.

EXPERIMENTAL EXAMPLE 1

50 μl of 1% hydrochloric acid solution was applied by spraying on each 1 kg of various commercial starches and mixed evenly by means of a mixer, placed on an aluminum vat, pre-dried for 1 hour in a drier, then heated at a temperature of 150° C. for 2 hours. Warm water at a 2:1 ratio to pyrodextrin was added to each pyrodextrin and neutralized to pH 5.8 with 1N sodium hydroxide; then 0.1% "Termamyl" was added to each solution to react at a temperature of 95° C. for 1 hour, and further heated to 115° C. to complete the reaction. Subsequently, each solution was filtered and decolorized and concentrated in vacuo to a concentration of 30%. Thereafter, caloric value of each solution together with intermediate products was determined, and transparency of each sample solution was measured. Table 1 shows the result.

TABLE 1

| Material starches | Potato starch | Tapioca | Corn starch |
|---|---|---|---|
| Kcal/100 g of pyrodextrin | 226 | 253 | 246 |
| Kcal/100 g after hydrolysis with alpha-amylase | 235 | 259 | 250 |
| Transparency of solution after refining | transparent | transparent but reddish | opaque |

EXPERIMENTAL EXAMPLE 2

50 ml of 1% hydrochloric acid solution was applied by spraying on each 1 kg of commercial potato starches and mixed evenly by means of a mixer, placed on an aluminum vat, pre-dried for 1 hour in a drier, then heated at a temperature of 150° C. for 5 hours while picking up 800 g of sample every hour. Warm water at a 2:1 ratio to pyrodextrin was added to each pyrodextrin and neutralized to pH 5.8 with 1N sodium hydroxide; then 0.1% "Termamyl" was added to each solution to react at a temperature of 95° C. for 1 hour, and further heated to 115° C. to complete the reaction. Subsequently, the solution decolorized and filtered by conventional methods was subject to a deionization test using mixed bed ion exchange resins. Indication of successful deionization occurs when chloride leaks into the effluent. Caloric value of the deionized solution was determined after being concentrated in vacuo to 30%, and flavor of each solution was measured by sensory test. Table 2 shows the result.

TABLE 2

| Heating time | 1 | 2 | 3 | 4 | 5 |
| --- | --- | --- | --- | --- | --- |
| Amount of deionized effluent by ion exchange resin (ml/ml resin) | 7.31 | 5.54 | 4.30 | 3.71 | 2.69 |
| Kcal/100 g | 329 | 286 | 232 | 223 | 217 |
| Flavor (stimulant taste) | good | good | good | good | excessively stimulative |

EXPERIMENTAL EXAMPLE 3

0.1% "Klaistase KD" was added to each 400 g of pyrodextrin obtained in the foregoing Example 2 and reacted at 85° C. Other treatments and conditions were the same as those described above. Table 3 shows the result of determination of caloric values.

TABLE 3

| Heating time | Kcal/100 g |
| --- | --- |
| 1 | 325 |
| 2 | 301 |
| 3 | 250 |
| 4 | 244 |
| 5 | 243 |

It is understood from Table 1 that caloric value of 3 kinds of starches are more or less 250 Kcal/100 g; that a transparent solution can be obtained when using potato starch; that use of tapioca starch results in a reddish solution; and that the solution using corn starch is opaque. This means that the latter two starches are not suitable for food.

However, when extracting digestive fractions using ion exchange resins chromatography or organic solvent method by reacting glucoamylase on aqueous solution of pyrodextrin after reacting alpha-amylase thereon, then filtering and refining it by conventional methods, the colored and/or opaque substances can be removed, and therefore starch other than potato starch, such as corn starch, can also be employed as a raw material.

It is also understood from Table 2 that, though caloric value reduces in proportion to the length of heating time, capacity of ion exchange resin reduces here caloric value comes down to less than 220 Kcal/100 g. Since the capacity is one of the important steps in refining process, such reduction of capacity is not desirable for mass production, and moreover there arises a further disadvantage of stimulative taste impossible to remove even by ion exchange resin.

Comparing the caloric values between Tables 2 and 3, it is understood that lower calories are achieved in the dextrin prepared by adding "Termamyl", and therefore it is obviously preferable to use "Termamyl", as far as caloric value is in the mentioned range of 220 to 280 Kcal/100 g. In addition, measurement of the caloric value was carried out in the same manner as a later described embodiment.

Note that the low calorie dextrin achieved in accordance with the invention can be desirably applied to a variety of foods including, but not limited to, breads and confectionaries such as cookies, doughnuts, cakes, breads; creams such as custard cream, cream, butter cream; and a variety of other foods such as chocolate, chewing gum, pudding, Bavarian, jelly, yoghurt, ice cream, juice, milk shake.

DESCRIPTION OF THE PREFERRED EMBODIMENTS

Several embodiments in accordance with the present invention is hereinafter described. In these embodiments, measurement of caloric values were carried out in the following method.

1. Method for measuring caloric value

The effective caloric value of a sample was calculated as the sum of the caloric value resulting from digestion and absorption by the digestive system up to the upper digestive tract, and the caloric value resulting from intestinal fermentation after the arrival of the sample at the large intestine.

Test 1 : Measurement of caloric value resulting from digestion and absorption by the upper digestive tract up to the small intestine The sample was dissolved in 45 mM (bis)Tris buffer (pH 6.0) containing 0.9 mM calcium chloride to obtain a 4.55% solution, to which 160 U/g human salivary alpha-amylase (SIGMA Type IX-A) was added, followed by a reaction at 37° C. for 30 minutes. After deactivating the enzyme, the reaction mixture was desalted with an ion exchange resin and adjusted to a concentration of 1.1%. The aqueous solution (4 ml) was then added to 2 ml of 50 mM hydrochloric acid-potassium chloride buffer (pH 2.0), and the mixture was maintained at 37° C. for 100 minutes, followed by desalting with an ion exchange resin.

To the desalted solution was added 45 mM (bis)Tris buffer (pH 6.0) containing 0.9 mM calcium chloride to adjust the solution to a concentration of 0.45%. To the solution was added 400 U/g of porcine pancreatic amylase (product of Yamanouchi Co., Ltd), followed by a reaction at 37° C. for 6 hours. The enzyme was then deactivated, and the reaction mixture was thereafter desalted with an ion exchange resin, concentrated and freeze-dried.

The powdery sample thus obtained was dissolved in 45 mM sodium maleate buffer (pH 6.6) to prepare a 0.45% solution, with which 86 U/g or rat small intestine mucous membrane enzyme (product of SIGMA) was reacted at 37° C. for 3 hours. The amount of glucose produced was determined by the pyranose oxidase method. The caloric value to be produced by digestion and absorption was calculated from the following equation.

$$\text{Caloric value} = \frac{\text{Amount of glucose produced (\%)} \times 4\text{Kcal/g}}{100}$$

Test 2: Determination of caloric value resulting from intestinal fermentation

The caloric value of the fraction reaching the large intestine was determined by the growth curve method using rats as described below.

TABLE 4

| Component | Ratio |
| --- | --- |
| Corn starch | 42.7 |
| Casein | 40.0 |
| Fiber | 2.0 |
| Mineral mixture | 10.0 |
| Vitamin mixture | 0.8 |
| DL-Methionine | 0.3 |
| Choline bitartrate | 0.2 |
| Vegetable oil | 5.0 |

Rats were preliminarily raised for 5 days to adapt them to the laboratory environment and to the basal diet shown in Table 4, then checked for the body weight and health and divided into groups (10 rats in each group). The average initial body weight of all the test groups was 79.6 to 80.8 g. The body weight variations of the groups were in the range of 9 to 16 g. The caloric value of all the test components and basal diet were measured by bomb-calorimeter.

TABLE 5

| No. | Base diet (g) | Glucose (g) | Sample (g) | Total amount (g) | Calorific value kcal/g |
|---|---|---|---|---|---|
| 1 | 5.4 | — | — | 5.4 | 22.7 |
| 2 | 5.4 | 0.5 | — | 5.9 | 24.7 |
| 3 | 5.4 | 1.0 | — | 6.4 | 26.7 |
| 4 | 5.4 | 2.0 | — | 7.4 | 30.7 |
| 5 | 5.4 | 4.0 | — | 9.4 | 38.7 |
| 6 | 5.4 | — | 0.5 | 5.9 | 24.7 |
| 7 | 5.4 | — | 1.0 | 6.4 | 26.7 |
| 8 | 5.4 | — | 2.0 | 7.4 | 30.7 |
| 9 | 5.4 | — | 4.0 | 9.4 | 38.7 |

After grouping, the rats were placed into individual steel cages and fed according to the experimental schedule listed in Table 5. The basal diet was fed to all rats in an amount of 5.4 g/rat/kg (22.7 kcal/rat/day). For the test groups, glucose or the above sample was added in an amount of 0.5, 1.0, 2.0 or 4.0 g to the basal diet. The amount of glucose or sample added was about 2, 4, 8 or 16 kcal/rat/day in terms of caloric value. The amount of ingestion was measured daily, and the gain in the body weight was measured on the start day, 5th, 10th and 15th days. The rats were checked generally every day by observation.

Table 6 shows the results.

TABLE 6

| No. | Initial body weight (g) | Final body weight (g) | Gain g/14 days | Calories consumed kcal/day | Calories required for 1 g gain |
|---|---|---|---|---|---|
| 1 | 80.8 | 67.3 | −13.5 | 22.7 | — |
| 2 | 80.5 | 72.9 | −7.6 | 24.8 | — |
| 3 | 80.7 | 79.0 | −1.7 | 26.2 | — |
| 4 | 80.2 | 90.1 | 9.9 | 30.3 | 0.023 |
| 5 | 80.3 | 106.4 | 26.1 | 36.7 | 0.051 |
| 6 | 80.2 | 72.0 | −8.2 | 24.8 | — |
| 7 | 79.6 | 75.1 | −4.5 | 26.2 | — |
| 8 | 80.4 | 86.1 | 5.7 | 31.1 | 0.013 |
| 9 | 79.9 | 84.7 | 4.8 | 39.8 | 0.009 |

With reference to Table 6, the caloric value determined by the animal experiment is:

(0.013÷0.023×3.8+0.009÷0.051×3.8)÷2×1.41 kcal/g

From Test 1, the caloric value resulting from the digestion and absorption of the sample by the upper digestive tract is:

$$\frac{9.8 \times 4\text{kcal/g}}{100} = 0.39 \text{kcal/g}$$

Accordingly, the caloric value resulting from intestinal fermentation is:

1.41−0.39=1.02 kcal/g

From this data, the caloric value produced by the intestinal fermentation of the dextrin is: 1.02÷0.912 (proportion reaching the large intestine)=1.1 kcal/g=about 1 kcal/g Thus, according to the methods of Test 1 and Test 2, the caloric value was calculated from the following equation.

$$\text{Caloric value (kcal/g)} = \frac{\text{Glucose produced (\%)} \times 4}{100} + \frac{(100 - \text{glucose produces (\%)}) \times 1}{100} = 1 + \frac{3 \times \text{glucose produced (\%)}}{100}$$

EXAMPLE 1

2500 kg of potato starch was put into a Ribbon Mixer, 250 liters of 1% hydrochloric acid was sprayed with compressed air while rotating the mixer, and after being uniformized through a disintegrator, further allowed to age in the Ribbon-mixer for 10 hours. The obtained mixture was pre-dried to 3% moisture, subsequently put into a Rotary-Kiln-Type converter to be continuously heated at a temperature of 180° C. for two hours. It was acknowledged that the pyrodextrin thus obtained having a caloric value of 228 kcal/100 g.

4000 liters of water was added to this pyrodextrin and its pH adjusted to 6.0 by adding 20% sodium hydroxide, then 0.2% by weight dry solids of the solution of alpha-amylase (Termamyl 60L produced by Novo Inc.) was added to hydrolyze at a temperature of 95° C. for 1 hour. Most of the solution was then refined through conventional processes such as decoloring and filtration with activated charcoal, deionization with ion exchange resins, and subsequently spray dried. Thus, about 1800 kg of dextrin having a caloric value of 226 kcal/100 g was obtained.

EXAMPLE 2

About 100 liters of residual solution hydrolyzed with alpha-amylase in the foregoing Example 1 was heated at a temperature of 55° C., with its pH adjusted to 5.5, and saccharified by adding 0.1% by weight of glucoamylase (produced by Amano Seiyaku Co.). The pH was then adjusted to 3.5 and reaction of glucoamylase was terminated. After refining in the same manner as Example 1, 60kg of 50% solution was obtained through concentration. 100 liters of this solution was applied, at S.V.=0.25, to a column packed with "XFS-43279.00" (produced by Dow Chemical Japan), an alkali metal type strongly acidic cation exchange resin, then the high molecular weight dextrin was extracted by applying water, and, after concentration, a dextrin having a caloric value of 128 kcal/100 g was obtained by spray drying.

EXAMPLE 3

25 liters of 95% ethanol were added to 1 liter of 50% concentrated solution obtained in Example 2 while being stirred, then left for 1 hour, centrifugated to separate the precipitates, dried in vacuo at 70° C., with dried dextrin solid obtained.

EXAMPLE 4

2500 kg of commercial corn starch was put into a ribbon mixer. 250 liters of 1% hydrochloric acid solution was sprayed using compressed air while rotating the mixer. After uniformized by a disintegrator, the mixture was aged for 10 hours. After pre-drying the mixture to be about 4% moisture by a flash drier, the mixture was consecutively put in Rotary-Kily-Type converter and heated at 180° C. 2 hours. Caloric value of the pyrodextrin thus obtained was 238 kcal/100 g per solid. Then, a solution of this pyrodextrin was heated to 55° C., with its pH adjusted to 5.5, and saccharified by adding 0.1% by weight of glucoamylase (produced by Amano Seiyaku Co.). The pH was then adjusted to 3.5 and reaction of glucoamylase was terminated. Then, after refining through conventional processes of decoloring and filtration with activated charcoal and deionization with ion exchange resins, the solution was concentrated to 50% and applied, at S.V.=0.25, to a column packed with 2500 liters of "XFS-43279.00" (produced by Dow Chemical Japan), which was an alkali metal type strongly acidic cation exchange resin, the high molecular weight dextrin was extracted by applying water, and after concentration, a dextrin having a caloric value of 129 kcal/100 g was obtained by spray drying.

What is claimed is:

1. A method for preparing low calorie dextrin of which the caloric value is not more than 220 Kcal/100 g which comprises the steps of:

heating corn starch in the presence of a mineral acid to prepare pyrodextrin, hydrolyzing the pyrodextrin with α-amylase, adding an organic solvent to the hydrolyzed pyrodextrin to dissolve low molecular weight digestible components and recovering low calorie dextrin from the solvent-treated pyrodextrin.

2. The method of claim 1, wherein said low calorie dextrin is obtained by heating said corn starch in the presence of hydrochloric acid in an amount of 0.01 to 0.1% by weight based on the weight of said corn starch at 150° C. to 220° C. for 1 to 5 hours to prepare pyrodextrin, dissolving the pyrodextrin in water to form an aqueous solution in an amount of 30 to 45% by weight of pyrodextrin based on the weight of the solution, adjusting the pH of the solution to pH 4.5 to 6.5, treating the solution with α-amylase in an amount of 0.05 to 0.2% by weight based on the weight of the pyrodextrin at 85° C. to 100° C. for 0.5 to 2 hours, treating the solution with glucoamylase in an amount of 0.05 to 0.2% by weight based on the weight of the pyrodextrin at about 55° C. for 24 to 48 hours, adding the organic solvent to the thus treated pyrodextrin to dissolve low molecular weight digestible components and recovering low calorie dextrin from the solvent-treated pyrodextrin.

3. The method of claim 1, wherein said organic solvent is ethanol.

* * * * *